United States Patent [19]

Semancik et al.

[11] Patent Number: 5,345,213
[45] Date of Patent: Sep. 6, 1994

[54] TEMPERATURE-CONTROLLED, MICROMACHINED ARRAYS FOR CHEMICAL SENSOR FABRICATION AND OPERATION

[75] Inventors: Stephen Semancik, Mt. Airy; Richard E. Cavicchi, Washington Grove; Michael Gaitan, Gaithersburg; John S. Suehle, Westminister, all of Md.

[73] Assignee: The United States of America, as represented by the Secretary of Commerce, Washington, D.C.

[21] Appl. No.: 965,949

[22] Filed: Oct. 26, 1992

[51] Int. Cl.$^5$ .................... H01C 7/00; H01C 1/012
[52] U.S. Cl. .................... 338/34; 338/307; 257/253; 437/918
[58] Field of Search .................... 338/34, 35, 307, 25; 257/253, 252; 73/31.05, 31.06; 422/98, 90; 436/149, 113, 150, 151; 437/918, 248, 60

[56] References Cited

U.S. PATENT DOCUMENTS

| | | |
|---|---|---|
| 3,509,431 | 4/1970 | Iles et al. |
| 3,571,917 | 3/1971 | Merryman et al. |
| 4,103,073 | 7/1978 | McAlear et al. |
| 4,142,925 | 3/1979 | King et al. |
| 4,181,544 | 1/1980 | Cho |
| 4,286,377 | 9/1981 | Hurko et al. |
| 4,292,730 | 10/1981 | Ports |
| 4,425,379 | 1/1984 | Vora et al. |
| 4,470,875 | 9/1984 | Poteat |
| 4,542,640 | 9/1985 | Clifford .................... 73/31.06 |
| 4,574,264 | 3/1986 | Takahashi et al. |
| 4,612,083 | 9/1986 | Yasumoto et al. |
| 4,636,767 | 1/1987 | Barger et al. .................... 338/34 |
| 4,701,739 | 10/1987 | Sasaki .................... 338/34 |
| 4,728,591 | 3/1988 | Clark et al. |
| 4,743,954 | 5/1988 | Brown |
| 4,816,800 | 3/1989 | Onaga et al. .................... 338/34 |
| 4,824,803 | 4/1989 | Us et al. |
| 4,892,834 | 1/1990 | Rauh .................... 73/31.06 X |
| 4,897,361 | 1/1990 | Harriott et al. |
| 4,897,814 | 1/1990 | Clark |
| 4,918,032 | 4/1990 | Jain et al. |
| 4,985,373 | 1/1991 | Levinstein et al. |
| 5,019,885 | 5/1991 | Yagawara et al. |
| 5,050,091 | 9/1991 | Rubin |
| 5,071,770 | 12/1991 | Kolesar, Jr. |
| 5,075,250 | 12/1991 | Hawkins et al. |
| 5,131,954 | 7/1992 | Vogeli et al. |
| 5,140,393 | 8/1992 | Hijikihigawa et al. .................... 257/252 |
| 5,143,696 | 9/1992 | Haas et al. .................... 422/98 X |
| 5,185,130 | 2/1993 | Camanzi et al. .................... 422/98 X |

(List continued on next page.)

OTHER PUBLICATIONS

N. Yamazeo and T. Seiyama, Proc. of the 3rd Int'l. Conf. on Solid State Sensors and Actuators (IEEE, Philadelphia, 1985), p. 376.
P. T. Mosely and B. C. Tolfield, Solid State Gas Sensors (Adam Hilger, Bristol, 1987).
S. R. Morrison, Proc. of the 2nd Int'l. Meeting on Chemical Sensors (Bordeaux, 1986), p. 39.
J. F. McAleer, P. T. Moseley, J. O. W. Morris and D. E. Williams, J. Chem. Soc. Faraday Trans. I 83, 1323 (1987).
A. Ikegami and M. Kaneyasu, 1985 Digest of Technical Papers, Int. Conf. Solid State Sensors and Actuators, "Transducers 85", IEEE (Library of Congress 84-62799) p. 74.

(List continued on next page.)

Primary Examiner—Marvin M. Lateef
Attorney, Agent, or Firm—Michael S. Gzybowski

[57] ABSTRACT

Planar forms of chemically-sensitive materials have been combined, under temperature control, with the pixels of a specially-designed micro-hotplate array to produce a miniature device capable of analyzing chemical mixtures. The device uses integrated multiple elements having different adsorption properties and temperatures to collectively achieve chemical selectivity in sensing. The method of making and using selectively in sensing. The device of the present invention is manufactured by standard CMOS foundry techniques which allow the production of a range of devices that have improved sensing performance.

28 Claims, 7 Drawing Sheets

OTHER PUBLICATIONS

Chang et al., (S. C. Chang and D. B. Hicks, 1985 Digest of Technical) Papers, Ind. Conf. Solid State Sensors and Actuators, "Transducers 85", IEEE (Library of Congress 84–62799) p. 381.

Wang, et al., (X. Wang, S. Yee, and P. Carey), Proc. of the 1992 IEEE Workshop on Sensors (Hilton Head, 1992), p. 23.

Najafi et al. (N. Najafi, K. D. Wise, R. Merchange and J. W. Schwank), Proc. of the 1992 IEEE Workshop on Sensors (Hilton Head, 1992), p. 19.

M. Parameswaran et al., "Micromachined Thermal Radiation Emitter from a -Commercial CMOS Process", *IEEE Electron Device Letters*, vol. 12, No. 2 (1991) pp. 57–60.

Jaeggi et al., "Thermoelectric AC Power Sensor by CMOS Technology", *IEEE Electron Device Letters*, vol. 13, No. 7 (1992), p. 366.

TEMPERATURE-CONTROLLED, MICROMACHINED ARRAYS FOR CHEMICAL SENSOR FABRICATION AND OPERATION

TECHNICAL FIELD

The present invention relates to temperature-controlled sensors and processes for making and using the same. More particularly, the present invention relates to temperature controlled chemical sensors which are made by micromachining techniques and method of using the same.

BACKGROUND ART

Various types of solid state gas sensors have been in use for decades for applications where their performance is deemed adequate for a given task as reported by Yamazoe et al (N. Yamazoe and T. Seiyama, Proc. of the 3rd Int'l. Conf. on Solid State Sensors and Actuators (IEEE, Philadelphia, 1985) p. 376). Examples of such gas sensors include devices that detect unsafe levels of poisonous or explosive gases in work environments as well as sensors that measure humidity or contaminants within process gas streams. However, performance problems, particularly those related to poor stability, slow response time and interference effects from constituents other than those being measured, have been known to severely limit the utility of chemical sensors ( P. T. Moseley and B. C. Tofield, Solid State Gas Sensors (Adam Hilger, Bristol, 1987)). A similar scenario exists for sensors that are used for composition and concentration measurements in solutions.

While sensors operate on a variety of principles, they all depend on the occurrence of chemical interaction between the probed environment and the active portion of the sensor to produce a sensor signal that can be interpreted to provide specie(s) concentration(s). A certain, but limited level of selectivity can be introduced in sensors by altering the type of active material employed as reported by Morrison (S.R. Morrison, Proc. of the 2nd Int'l. Meeting on Chemical Sensors (Bordeaux, 1986), page 39). It is also recognized that temperature changes can affect the solid state devices by altering interaction kinetics and other properties (J.F. McAleer, P.T. Moseley, J.O.W. Norris and D.E. Williams, J. Chem. Soc. Faraday Trans. I 83, 1323 (1987)).

In many cases, single active sensing elements are applied, but the literature has been increasingly reporting results from developmental work on integrated element array devices which produce multiple outputs that are analyzed by known pattern recognition techniques.

Various structures have been micromachined for use in sensing. Ikegami and Kaneyasu describe an integrated sensor array of 6 elements that uses pattern recognition techniques to identify gases such as ammonia, menthol, and hydrogen sulfide (A. Ikegami and M. Kaneyasu, 1985 Digest of Technical Papers, Int. Conf. Solid State Sensors and Actuators, 'Transducers 85' IEEE (Library of Congress 84-62799) p. 74). The array is fabricated on alumina, and is not adaptable to the use of Si micromachining techniques. The heater for the sensor array is a single large structure which is applied to all the elements simultaneously. Therefore, the elements can not be individually temperature controlled.

Chang et al (S.C. Chang and D.B. Hicks, 1985 Digest of Technical Papers, Int. Conf. Solid State Sensors and Actuators, 'Transducers 85' IEEE (Library of Congress 84-62799) p. 381) describe an integrated sensor with an integrated heater element fabricated using Si integrated circuit thin film techniques. This sensor does not, however, have good thermal isolation from the rest of the chip. Because of this, it does not respond rapidly to temperature changes and requires a substantial amount of power to operate. In addition, this device does not include a separate layer for temperature measurement and heat dispersal. Therefore, temperature measurements which are effected by monitoring the heater resistance are not accurate.

Wang et al (X. Wang, S. Yee, and P. Carey, Proc. of the 1992 IEEE Workshop on Sensors (Hilton Head, 1992) p. 23) describe an array of sensor elements fabricated on Si membranes produced by micromachining technology. The technique used to create the sensor, however, requires aligning an etch of the back side of a Si wafer with sensor structures on the front side. This requires special photolithography techniques, which are not compatible with the processes available at commercial foundries and is therefore is more expensive to set up. There is no separate temperature sensing layer provided in the device of Wang et al. Moreover, the fabrication methods described do not include the possibility of using the integrated heater to process the sensing materials grown above it. Finally, no consideration is given to novel temperature programming techniques to enhance response.

Najafi et al (N. Najafi, K.D. Wise, R. Merchant and J.W. Schwank, Proc. of the 1992 IEEE Workshop on Sensors (Hilton Head, 1992), p. 19) describe an integrated multi-element gas analyzer created by micromachining technology using an integrated heater, silicon resistor temperature sensors, and sensing film with four contacts. The fabrication technique used here also involves a backside etch of the Si wafer, with the equipment expense problems and alignment difficulties associated with the topside sensing elements. The temperature measurement is done using resistors which are interdigitated with the heaters, and so may give higher temperatures than are at the actual sensing surface. Again, the fabrication methods described do not include the possibility of using the integrated heater to process the sensing materials grown above it. Although temperature ramps are used as a part of a sensing process, there is no mention of the use of very rapid, i.e., from 1 msec to 1 sec, temperature pulses to enhance sensing response and device performance.

The present invention uses both chemically-tuned elements and temperature variation to achieve superior sensing performance, especially with respect to analyzing mixtures. During the course of the present invention, new technology was developed which combines the previously-recognized materials and temperature concepts with a unique micromachined hotplate array design in order to realize a commercially-viable miniature sensor for analyses of species mixtures.

DISCLOSURE OF THE INVENTION

It is accordingly one object of the present invention to provide a temperature controlled sensor element.

Another object of the present invention is to provide a temperature controlled sensor which includes an array of individually controlled sensor elements.

A further object of the present invention is to provide a temperature controlled sensor which includes an array of individually controlled sensor elements each having, as appropriate, a different chemical active sensing layer.

It is a further object of the present invention to provide a temperature controlled sensor which includes an array of individually controlled sensor elements having chemical and electrical behavior which are tuned to be responsive to a chemical specie(s).

A still further object of the present invention is to provide a method of fabricating a temperature controlled sensor elements in an array using the disclosed structure.

A still further object of the present invention is to provide a method of fabricating an array of individually controlled sensor elements each having a different chemical active sensing layer.

It is a still further object of the present invention to provide a method of fabricating an array of individually controlled sensor elements having chemical and electrical behavior which are tuned to be responsive to a chemical specie(s).

A yet further object of the present invention is to provide a method of selective chemical sensing which utilizes elements that are the same or different and which utilizes temperature schedules for each of the multiplicity of individual elements.

A yet further object of the present invention is to provide a device for chemical sensing which includes an array of sensor elements which are so small that the sensor elements do not suffer from consumption effects of species being monitored.

According to these and further objects of the present invention which will become apparent as the description thereof proceeds, there is provided a temperature-controlled sensor element which includes a support substrate;

a microbridge structure formed on the support substrate;

a heating element formed on the microbridge structure so as to be thermally isolated from the support substrate;

a conductive heat distribution plate formed above the heating element and;

a layer of chemical active material formed above the conductive heat distribution plate.

The present invention also provides for a temperature-controlled chemical sensor which includes:

an array of sensor elements positioned on a substrate support, wherein each of the sensor elements comprises:

a microbridge structure formed on the support substrate;

a heating element formed on the microbridge structure so as to be thermally isolated from the support substrate;

a conductive heat distribution plate formed above the heating element and; a layer of chemical active material formed above the conductive heat distribution plate.

The present invention further provides a method of making a temperature-controlled sensor element which comprises:

providing a support substrate having a first layer of an insulating material;

forming a microbridge structure on the support structure;

forming a heating element on the microbridge structure;

forming a second layer of insulating material on the heating element;

forming a conductive heat distribution plate on the second layer of insulating material;

forming a third layer of insulating material on the conductive heat distribution plate; and forming a layer of a chemical active material on the third layer of insulating material.

BRIEF DESCRIPTION OF DRAWINGS

The present invention will hereafter be described with reference to the annexed drawings which are given by way of non-limiting examples only in which.

BEST MODE FOR CARRYING OUT THE INVENTION

The sensor device of the present invention is based on a custom, monolithic structure which is fabricated by standard CMOS foundry techniques. This fact taken in combination with the commercially-viable planar deposition and thermal process control of sensing materials as described herein allows the sensor of the present invention to be easily adapted for production-scale manufacturing. In fact, many fabrication steps can be duplicated for multiple elements using planar deposition and lithography; such fabrication keeps production costs low. Since the device is fabricated using a MOSIS CMOS process, circuitry can be applied for on-chip signal handling.

According to a preferred embodiment, the device of the present invention is configured for sensing conductance of a chemical active material provided on the sensor. However, it is to be understood that other known methods of sensing changes of the chemical active material which are effected by exposure to a particular environment can be used including capacitance, I-V characteristics, work function, etc. The availability of many elements on a single sensing device as well as the fabrication methodology allow the invention to be specially customized to fit an extremely wide range of applications. In certain cases dedicated elements can be built into the device to serve as calibrator units or elements that monitor a particularly troublesome chemical interferant.

The present invention provides a thermal array sensing device capable of compositionally analyzing gas mixtures and other fluids and solutions when operated with known pattern recognition signal processing techniques. These "analyzers" can resolve compositions and concentrations at a much lower cost than instruments like gas chromatographs or mass spectrometers which are also much larger.

The present invention allows for sophisticated, individual temperature control of the multiple elements both during the fabrication of the sensing array (based upon temperature-dependent effects in deposition and post-processing active films) and during the operation of the multi-element sensor. Temperature control of the individual "pixels" or micro-hotplate devices including rapid temperature change allows compositional deconvolution to be performed using not only the varying adsorption and chemical properties of each active sensor film, but also the kinetic behavior of each of the elements during sensing. Predetermined temperature schedules and multiple pixels permit rapid optimization in the processing of film sensing materials (for developing and producing a wide range of sensors, based on, for example different crystalline orientation, microstructures or stoichimetry) and scientific studies of reaction and adsorption kinetics useful in sensing and other fields, including catalysis, corrosion, etc.

The individual elements of the sensors of the present invention can operate effectively at a very small size. By utilizing micromachining techniques to produce arrays of the sensors, it is possible to produce sensor arrays themselves which are very small. This means that the sensor arrays can be used in a highly nonobtrusive manner in a number of applications, including process control, pollution and safety monitoring. Many such applications require a small probe size or a device that does not distort flows or processing effects significantly. In addition to gas sensors, the devices of the present invention can be used for other types of chemical, biochemical and medical sensors. According to one embodiment, the materials of the base micromachined configuration could be adjusted so as to allow epitaxial growth of active sensing materials. This use of ordered and microstructure-controlled films can result in additional improvements in sensing performance.

The present invention is directed to sensor elements which comprise micro-hotplate devices or "pixels" (or "pixel substrates") upon which a film or layer of a chemical active material is positioned. Each of the micro-hotplates includes a heating element that is thermally isolated on a suspended membrane or micro-bridge and a conductive heat distribution plate which is above and electrically isolated from the heating element. The conductive heat distribution plate includes electrical leads which allow for temperature sensing and control.

A plurality of conductive pads, e.g. four, are provided above the conductive heat distribution plate, and are electrically isolated therefrom by an intermediate layer of insulation material. Another electrical insulation layer is provided over the conductive pads, with openings therein which allow each of the conductive pads to be exposed to the external or ambient environment. The conductive pads are used to sense properties of chemical active film layers which are formed thereon.

The micro-hotplates of the present invention are fabricated using standard CMOS compatible micromachine processes. To form the suspended membrane of microbridge structure, a wafer or chip of silicon which includes a top layer of an insulation material such as silicon dioxide is provided with openings in the top layer of insulating material so as to expose portions of the underlying silicon surface. These openings can be designed and implemented without any additional masking at any CMOS foundry. If the openings are properly laid-out according to the present invention, a suspended membrane or microbridge with support legs will be formed in a post-fabrication etch process described below.

According to the present invention, standard CAD software used to design devices and circuits to be manufactured in integrated circuit processes are used to design the micro-hotplate(s) of the present invention. Therefore, large numbers of the micro-hotplates can be designed and fabricated on a single support substrate, i.e. wafer or chip, using conventional CMOS techniques. There are a number of available software packages available which can be employed according to the present invention. One such software package which is available from the public domain and has been employed by the inventors during the course of the present invention is called MAGIC.

In order to use software packages such as MAGIC to design openings for the micromachining step, the technology file used in the software has to be modified. According to the modification, which is known and reported elsewhere (J. Marshall, M. Parameswaran, M. Zaghloul and M. Gaitan, "Methodology for the Computer-Aided Design of Silicon Micromachined Devices in a Standard CMOS Process", NISTIR, May 1992), a new layer, which in the present invention is referred to as "open" is formed. This layer is composed of IC fabrication masks that are available in standard CMOS processes but which are not normally used together, namely the glass cut, metal contacts, and poly and active area contacts. It is noted that while reference herein is made to the use of MAGIC, other CAD software packages could also be similarly modified in order to design the openings used in the present invention.

Figure 1A:
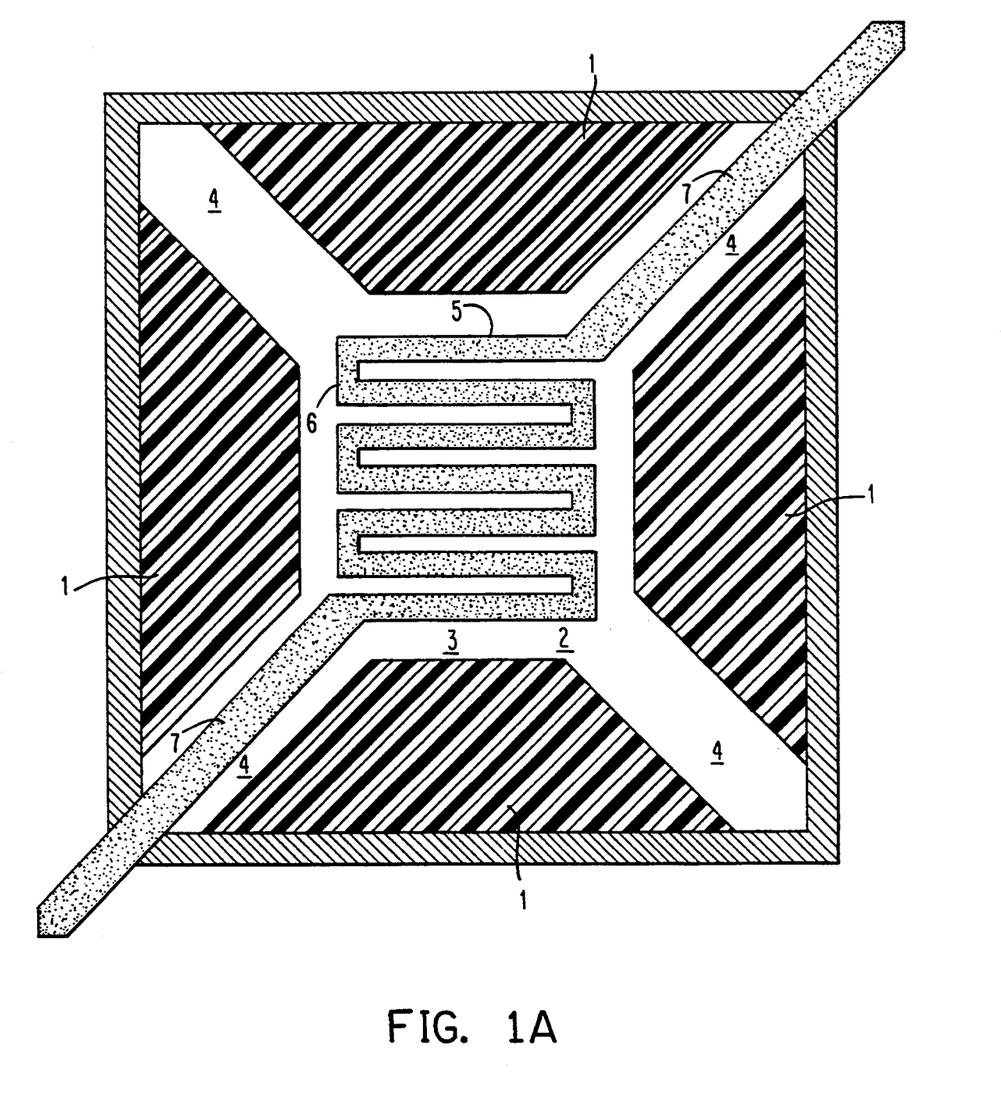
FIG. 1A is a schematic drawing showing the open areas and the heating element according to one embodiment of the present invention.

FIG. 1A shows the design of the openings and the heating element used according to one embodiment of the present invention. As shown in FIG. 1A, four openings 1 are provided along each side of the device of the present invention. The openings 1 expose the underlying silicon substrate, leaving a membrane or microbridge structure 2 which, after fabrication of the micro-hotplate(s) or pixel(s) is caused to be suspended by a post-fabrication etch process prior to applying the chemical active film layer(s) thereto. The post-fabrication etch process forms an etch pit 18 (FIG. 4) beneath the membrane or microbridge 2. In a preferred embodiment, the membrane or microbridge 2 is formed of an insulation material such as glass, e.g. silica, which provides mechanical support for the suspended structure and electrical insulation. The final suspended nature of the membrane or microbridge 2 itself provides thermal insulation of the device.

In FIG. 1A, the membrane or microbridge 2 is depicted as having a square central portion 3 and four support legs 4 which extend from corners of the central portion 3 to the edge of the device. The choice of design layouts for the openings 1 and resulting membrane or microbridge 2 is not limited to that shown in FIG. 1A. Other design layouts could also be used as long as they result in a suspended membrane or microbridge 2. For example, more or less than four support legs could be used to support a central membrane or microbridge portion. In this regard, a cantilevered structure could be used a well as a rectangular membrane which is supported at opposite ends to the edge of the device.

The heating element 5 shown in FIG. 1A includes a serpentine ribbon portion 6 of a conductive material which has leads 7 at opposite ends thereof. The leads 7 extend over the support legs 4 as shown. The heating element 5 functions as a resistive heater when an electrical current is applied to the leads 7 thereof. The heating element 5 can be made of any conductive material including metals or metalloids or compounds thereof. However, a polysilicon heating element was found to be particularly suitable for purposes of the present invention.

In addition to functioning as a source of heat, the heating element 5 can also be used to sense temperature in a known manner. Thus, according to one embodiment of the present invention, the heating element 5 can be used as a resistive heater and as a temperature, sensor. Accordingly to another embodiment of the invention, two separate parallel conductive lines are provided; one serving as a heater and the other serving as a temperature sensor.

Figure 1B:
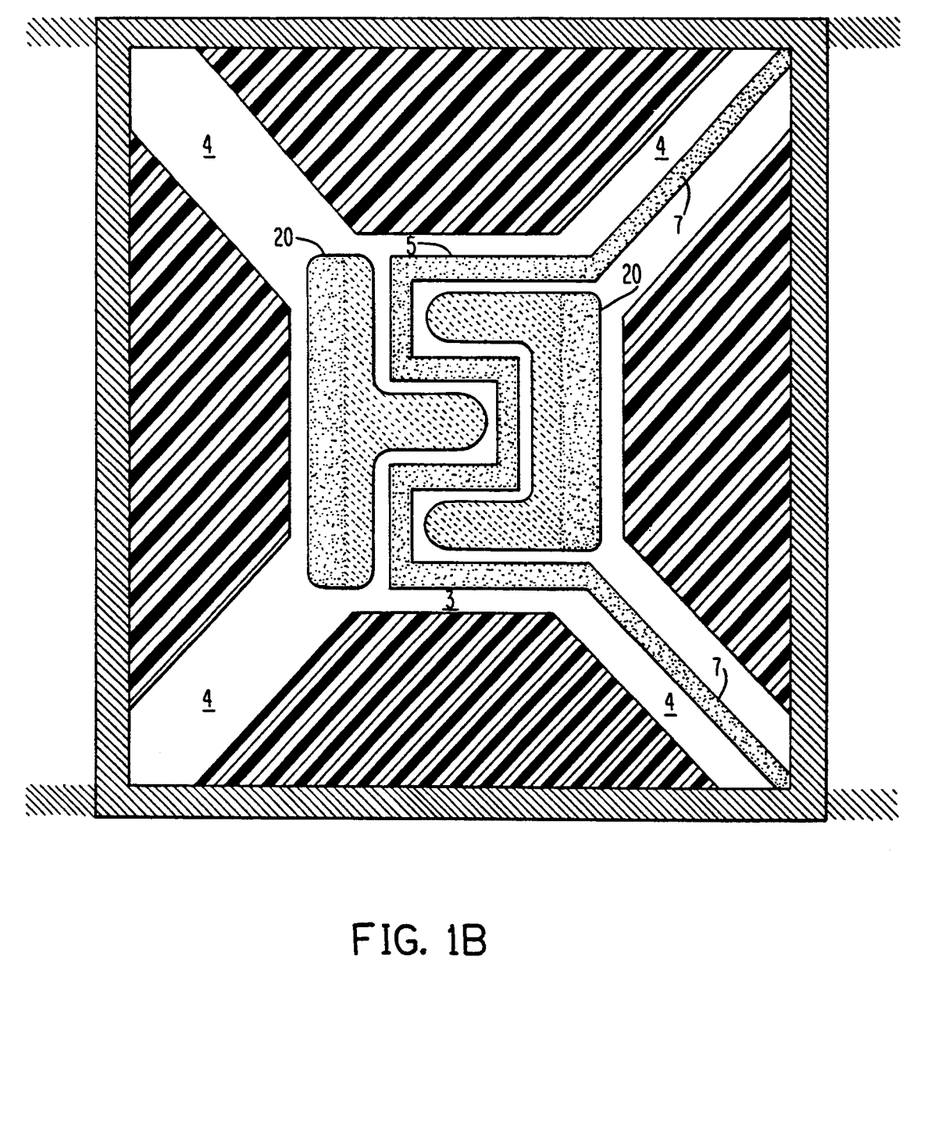
FIG. 1B is a schematic drawing showing an alternative embodiment of the heating element.

FIG. 1B is a schematic drawing showing an alternative embodiment of the heating element which includes adjacent, co-planar heat distribution elements or "islands". As depicted in FIG. 1B, the heating element 5 does not extend across the whole surface area of the central portion 3 of the membrane or microbridge 2. The surface area of the central portion 3 of the membrane or microbridge 2 which is not covered by the heating element 5 is provided with islands 20 of heat conducting material which are co-planar with the heating element 5. The material from which the heat conducting islands 20 are made can be the same or different from the material from which the heating element 5 is made. For example, both the heating element 5 and the heat conducting islands 20 can be made from polysilicon, which is thermally more conducting than silicon dioxide. The heat conducting islands 20 need not be connected to electrical leads. The heat conducting islands 20 can also be used in conjunction with the co-planar temperature sensor discussed above.

For convenience and cost consideration, all the materials used in the device of the present invention should be selected from those available from or compatible with standard CMOS processes. Commercial CMOS processes can be employed which can provide layers of polysilicon and aluminum; these processes can be used in known manners to fabricate the contacts, heaters, and temperature sensors used in the device of the present invention.

Figure 2:
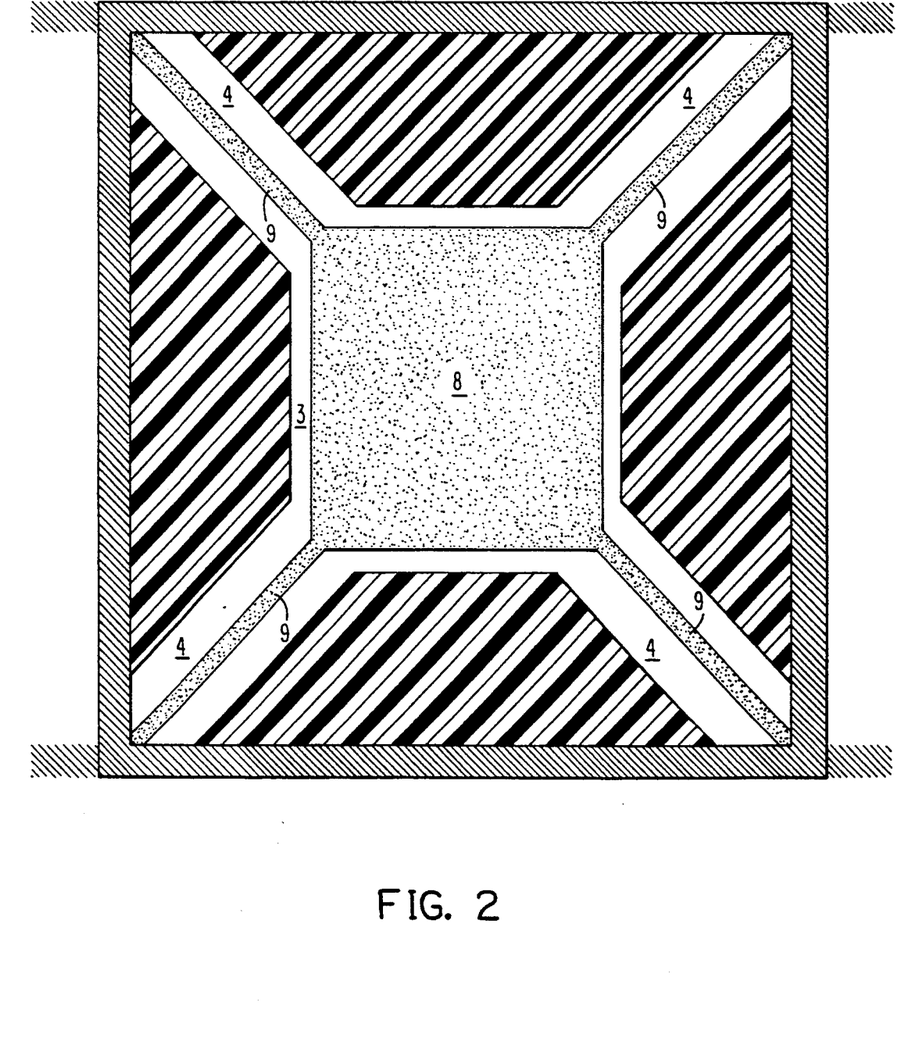
FIG. 2 is a schematic drawing showing the conductive heat distribution plate with four point contacts according to one embodiment of the present invention.

FIG. 2 shows the conductive heat distribution plate used in the micro-hotplate according to one embodiment of the present invention. The conductive heat distribution plate 8 is provided on top of the central portion 3 of the membrane or microbridge 2 and has a surface area which is preferable coextensive and aligned with the central portion 3 of the membrane or microbridge 2, or at least coextensive and aligned with the heating element 5, absent the leads thereof. The conductive heat distribution plate 8 and membrane or microbridge 2 are separated by a layer of insulating material 13 (FIG. 4) such as glass, e.g., silica, which provides electrical insulation therebetween. One of four leads 9 extend from each corner of the conductive heat distribution plate 8 on the support legs 4 as shown. These leads 9 allow for temperature sensing by measuring resistivity of the metallic heat distribution plate 8. In this regard, two of the leads are used for voltage sensing and the other two leads are used as current source lines in a conventional manner.

The conductive heat distribution plate 8 functions both to evenly distribute heat from the heating element 5 to the top surface of the micro-hotplate and as a means to sense temperature near the top surface. In this regard, the temperature is sensed by measuring the change in resistivity of the material from which the conductive heat distribution plate 8 is made as a function of temperature. This resistivity change is characterized by a term called the temperature coefficient of resistance, (TCR) and can be determined by measurements using an external hot plate as a reference in a conventional manner. The conductive heat distribution plate 8 can be made from any metal or metalloid or compounds thereof which conducts heat and can withstand temperatures at which the device is to be used. For purposes of the present invention aluminum was found to be a suitable material from which to make the conductive heat distribution plate 8. However, the conductive heat distribution plate 8 could be made from conductive materials having higher melting temperatures if the device is to be operated at high temperatures.

Figure 3:
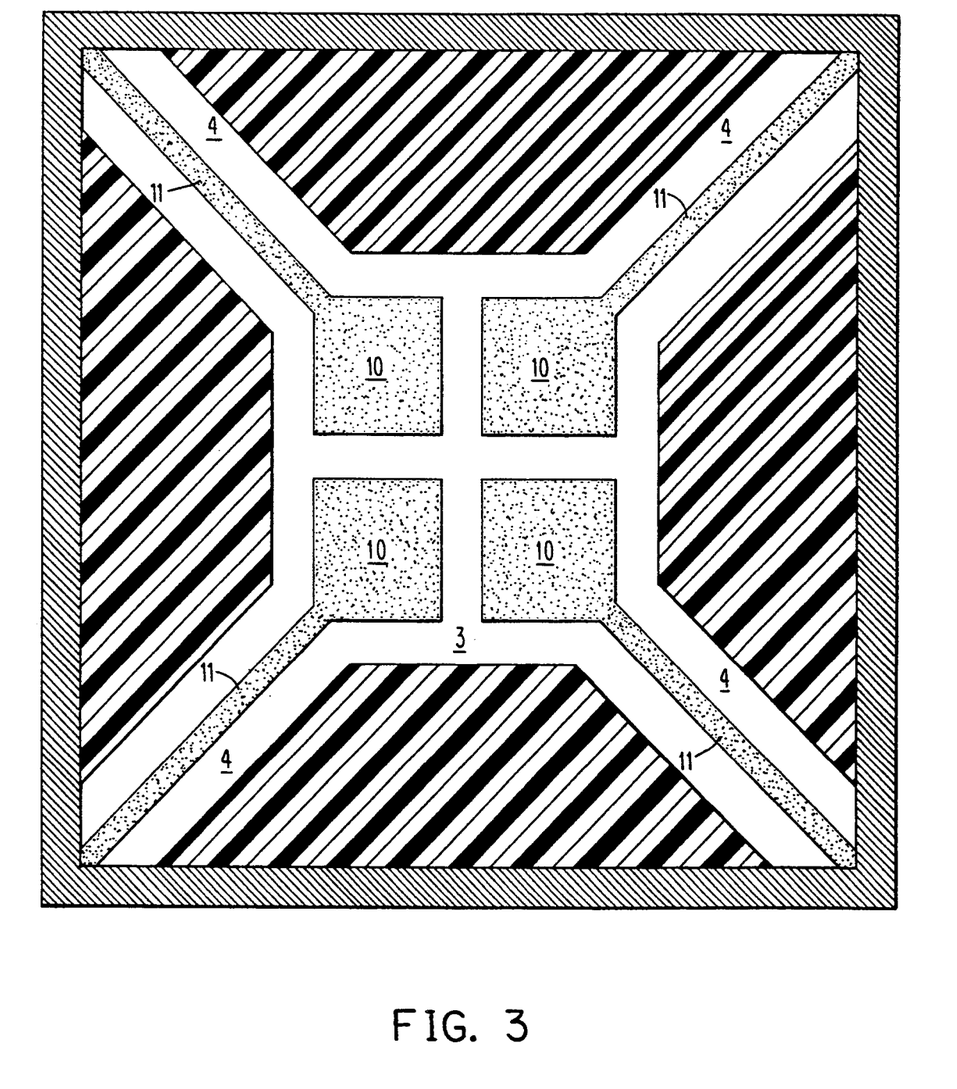
FIG. 3 is a schematic drawing of the contact pads according to one embodiment of the present invention.

FIG. 3 shows the contact pads upon which the chemical active film layer(s) is applied after the fabrication of the micro-hotplate(s) or pixel(s) is complete. As shown in FIG. 3 the contact pads 10 are symmetrically arranged over the conductive heat distribution plate 8. An electrical insulating layer 14 (FIG. 4) such as a glass, e.g., silica, is provided between the contact pads 10 and the conductive heat distribution plate 8. The contact pads 10 are covered by another layer 15 (FIG. 4) of an electrical insulating material such as glass, e.g., silica, which includes a like number of openings 16 (FIG. 4) that allow each of the contact pads 10 to be exposed to the chemical active film layer(s) which is applied as discussed below.

In operation, as discussed below, the contact pads 10, which are made form a conductive material such as metals or metalloids or compounds thereof, are used as point contacts to measure the electrical properties, i.e., resistance, of a chemical active film layer 19 (FIG. 4) formed on the contact pads 10 on the top of the device. For this purpose, conductive leads 11 extend from each of the contact pads 10 on the support legs 4 as shown. These leads could also be used in making other types of measurements.

Figure 4:
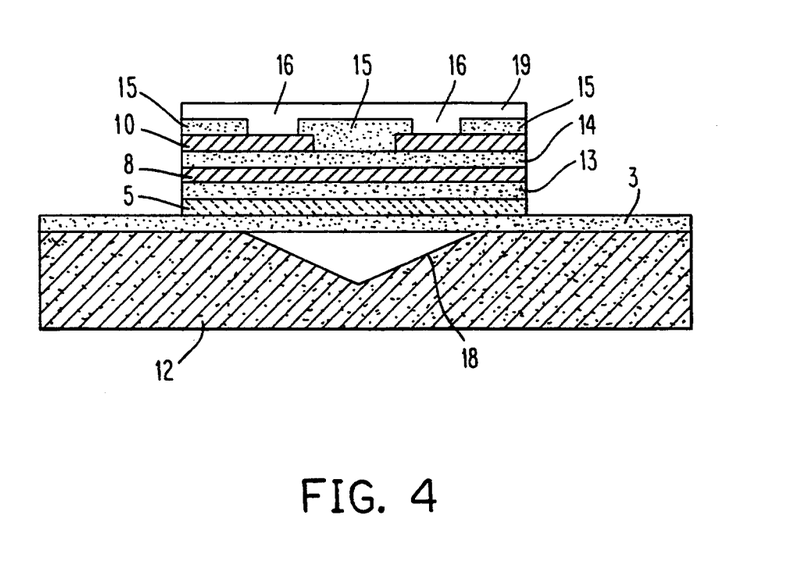
FIG. 4 is a schematic cross-sectional view of the micro-hotplate according to one embodiment of the present invention.

FIG. 4 is a schematic cross-sectional view of the micro-hotplate according to one embodiment of the present invention. As depicted in FIG. 4, according to a preferred embodiment, each micro-hotplate device has a suspended membrane or microbridge together with layers of polycrystalline silicon (PXS), silicon dioxide ($SiO_2$), aluminum (Al), and a chemical active film layer, e.g., $SnO_2$. These preferred materials, except for the chemical active film layer, are compatible with the CMOS processes used to fabricate the devices on the chip. The layer sequence on the silicon chip 12 from bottom to top as shown includes the suspended membrane or microbridge 2 which is made of silicon dioxide, the heating element 5 which is made of polycrystalline silicon, an insulating layer 13 of silicon dioxide, the conductive heat distribution plate 8 which is made of aluminum, another insulating layer 14 of silicon dioxide, four contact pads 10 which are made of aluminum, another insulating layer 15 of silicon dioxide with four openings 16 therein which communicate with the contact pads in the layer below and a chemical active film layer 19 of SnO$_2$.

While the devices of the present invention are designed by making use of standard CMOS compatible micromachine processes, CMOS foundries do not currently offer the additional post-fabrication etching step required to form the suspended membrane or microbridge structure of the present invention. Therefore, this step is carried out after the CMOS fabrication process, and before the chemical active film layer(s) is applied. This method of providing suspended membranes or microbridges has been shown to provide good thermal isolation in other devices (M. Parameswaran et al, "Micromachined Thermal Radiation Emitter from a Commercial CMOS Process", *IEEE Electron Device Letters*, Vol. 12, No. 2 (1991), pages 57–60).

After the designs are fabricated, the completed chips are subjected to a post-fabrication etch procedure to complete the fabrication of the device. In the post-fabrication etch a mixture of ethylenediamine-pyrocatechol-water-pyrazin (EDP, Transene Company) is utilized to form an etch pit 18 (FIG. 6) beneath at least the central portion 3 of the membrane or microbridge 2. EDP can be mixed in-house as reported in the literature (Jaeggi et al, "Thermoelectric AC Power Sensor by CMOS Technology", *IEEE Electron Device Letters*, Vol. 13, No. 7 (1992), page 366).

In the post-fabrication etch procedure used in the present invention aluminum hydroxide (AlOH) was added to the EDP in order to limit the attack of the EDP on exposed aluminum surfaces. The mixture was heated in a reflux container to 97° C. and the devices were etched for approximately 1 hour 15 minutes. After this step the fabrication is complete and the devices can be packaged and tested.

According to one embodiment, electroplating and electroless plating have been utilized to deposit barrier materials such as nickel and copper on exposed aluminum contact pads and on exposed silicon regions in order to protect these layers from the echant and to increase the operable temperature range of the device. This plating can be performed selectively on the contact pads, or the exposed silicon regions, or both utilizing maskless deposition techniques.

Thermal isolation which is provided for by the etching beneath the membrane or microbridge is necessary in order to heat the surface to elevated temperatures (in the range of ambient to over 1000° C.) at power levels that are compatible with IC-based applications (less than 100 mW per heater).

Thermal response time and power requirements of the device may be controlled by limiting or increasing the number and size of the legs 4 and the various electrical leads on the legs. In general, higher thermal conducting paths (more and/or shorter legs and more and-/or larger electrical leads) will provide a faster response time (on the order of one microsecond or less) at a higher power requirement. Fewer legs and less electrical leads will provide a lower power requirement, but a slower response time.

Devices have been fabricated which have a response time of about 1 millisecond and require 10 mW of power to attain a temperature of 500° C.

The contact pads are used according to a preferred embodiment of the present invention as discussed herein. However, since the conductive heat distribution plate is capable of measuring heat near the surface of the device, the contact pads can be eliminated when certain chemical active film layers are selected which can operate on adsorption/desorption principles to effect thermal characteristics of the device In such instances, the conductive heat distribution plate can be used to sense thermal changes and produce signals for identifying chemical species and compositions.

Figure 5:
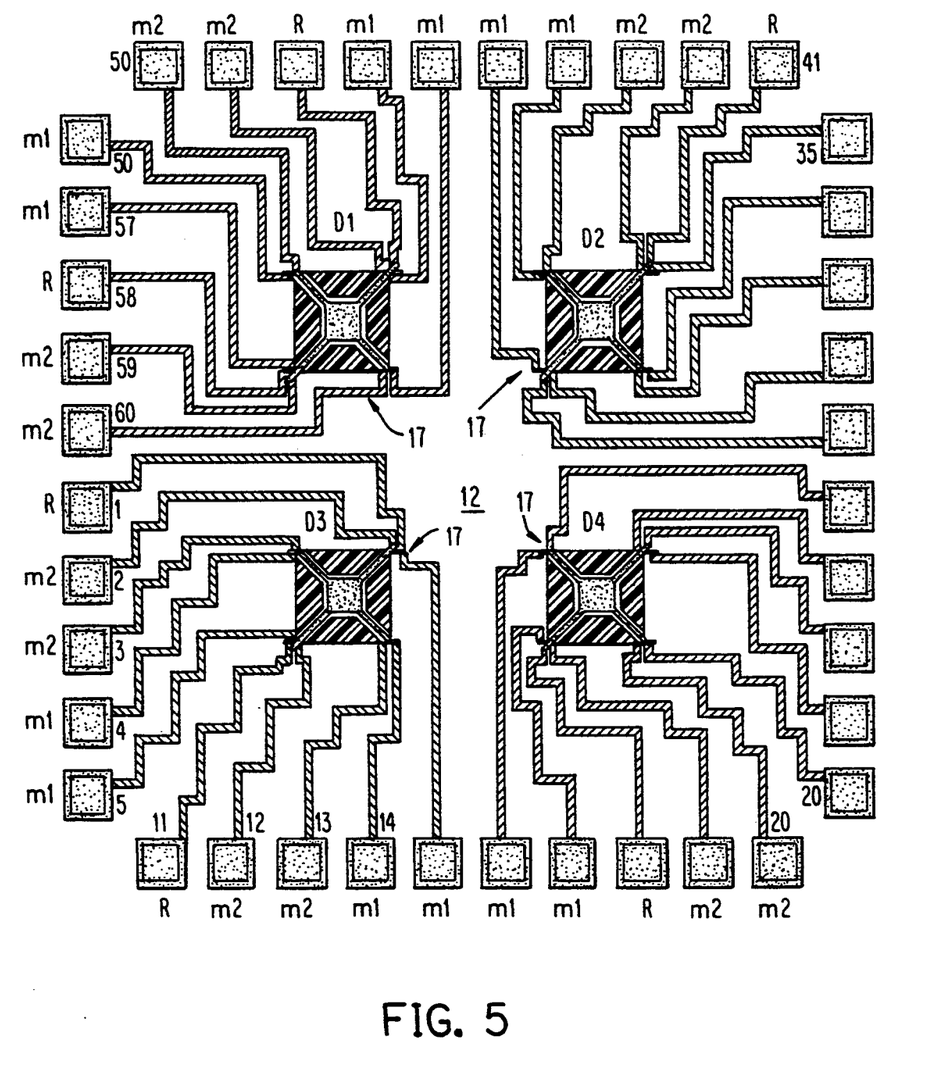
FIG. 5 is a schematic drawing of an array of four micro-hot plates on a single substrate according to the present invention.

FIG. 5 shows an array of four micro-hot plates on a single substrate according to the present invention. As shown in FIG. 5, the array includes a substrate support 12, e.g., a silicon chip, with an array of four micro-hotplates 17 with 10 leads per device. It is noted that while four micro-hotplates are shown in the array of FIG. 5, it is a simple matter to use the same technology to produce hundreds of similar devices on a single support substrate, i.e., a wafer or chip.

The micro-hotplate is heated by applying a suitable current of up to about 20 mA, and more typically about 4 mA to the leads 7 of the heating element 5. In response, the device heats up to a temperature related to the current. Temperature is measured by supplying a suitable current of up to about 50 mA, and more typically 10 mA, to two of the four leads 9 of the conductive heat distribution plate 8 and measuring the voltage drop, which is generally up to about 10 mV, and more typically about 1 mV, across the other two leads of the conductive heat distribution plate 8.

The device depicted in FIG. 4 and discussed above, has a operable temperature range of from ambient temperature (normally room temperature, although the chip may be mounted on a cold surface to obtain lower temperatures) to about 600° C. Above 600° C., aluminum begins to deform (by electromigration, etc.) and eventually melt. The device can be easily designed to operate at higher temperatures, e.g., up to 1200° C. by replacing the aluminum elements with polysilicon or other known high temperature resistive conductive materials.

Foundry processes that use metals other than aluminum, e.g., tungsten, will allow other metals to be used in the devices of the present invention and will provide micro-hotplates than can operate at much higher temperatures.

For clarity, the wire connections to each of the leads of the micro-hotplates has not been shown. However, in use, the chip supporting one or more micro-hotplates is mounted on a ceramic chip carrier, having conventional connections between the chip and carrier leads accomplished using gold wirebonds.

Sensors were formed by applying films of one or more chemical active material onto the top surface of the micro-hotplates, i.e., in contact with the contact pads. In an exemplary embodiment discussed herein, films of SnO$_2$ were applied to an array of micro-hotplates (hereafter referred as "pixels" or "pixel substrates"). For purposes of the present invention the term "chemical active" material refers to any type of layer for which a reaction may take place between the material film layer(s) and the fluids or materials to which the material film layer(s) is exposed, including adsorption/-desorption events which effect thermal properties, chemical reactions, including catalytic reactions, and biochemical reactions.

To vary film properties, different film thicknesses were deposited and different growth temperatures were utilized by varying the temperatures of the substrate pixels during film deposition. This was accomplished by having the device fully wired up within a deposition chamber, thereby allowing each pixel substrate to be thermally controlled. This procedure may be advantageous for some devices, however, is not a necessary step to produce an integrated gas sensor using the methodology described herein.

In addition to controlling the film properties during film deposition, the microstructure and precise composition of the $SnO_2$ (and other) films can also be altered following deposition by post-annealing any or all of the oxide-coated pixels individually. This temperature control capability is also applicable to other chemical modification procedures used to chemically-tune individual sensor elements, including controlling the growth of surface additive overlayers.

A number of lithographic methods were successfully used to spatially define the active sensing films in proper coincidence with all the pixels of an array. Photolithographic definition was carried out using photographic generation of a pattern to yield properly-sized windows over the pixel/contact areas. According to one embodiment, a photoresist (Shipley Resist 1470) was spun onto all sections of the device except the masked pixel areas prior to mounting the array device in the ultrahigh vacuum-based deposition chamber. This procedure was used in combination with a deposition and lift-off (chemical dissolving of the resist which lifts off the deposited film) approach to leave the active sensing films only at the pixel areas which did not have a photoresist coating.

Alternatively, maskless lithography can be carried out by spinning photoresist on all parts of the device and then volatilizing the coating off the pixel areas by heating each one (with its own heating element). This method then proceeded as above, with deposition and lift-off. Finally, for certain sensing materials (like $SnO_2$), no lithographic coatings may be required, since the entire device could be coated with a film which was inactive until heated above some temperature that changed a crucial property (like conductivity). In this last case, heating the covered pixels defined active sensing films only in the spatially-limited area above the pixel hotplate. While use can be made of only one active material, different films could be deposited on different ones of the pixel array elements.

Once the film (or films) is deposited on the pixels a wide range of process steps could be carried out to tune the chemical and electrical behavior of each array element. Vacuum annealing (to approximately 350° C.) was studied and found to be effective for tuning the chemical and electrical behavior of $SnO_2$ films. However, various other treatment procedures, including plasma reduction or oxidation, ion bombardment and deposition of metals, could be used for the tuning step. Temperature control may also be useful as part of these alternative procedures. Proper electrical connection into the vacuum-mounted array device using electrical feedthroughs and a wire-wrapped circuit holder was used for film deposition, post-processing and operation of the sensor device.

Figure 6:
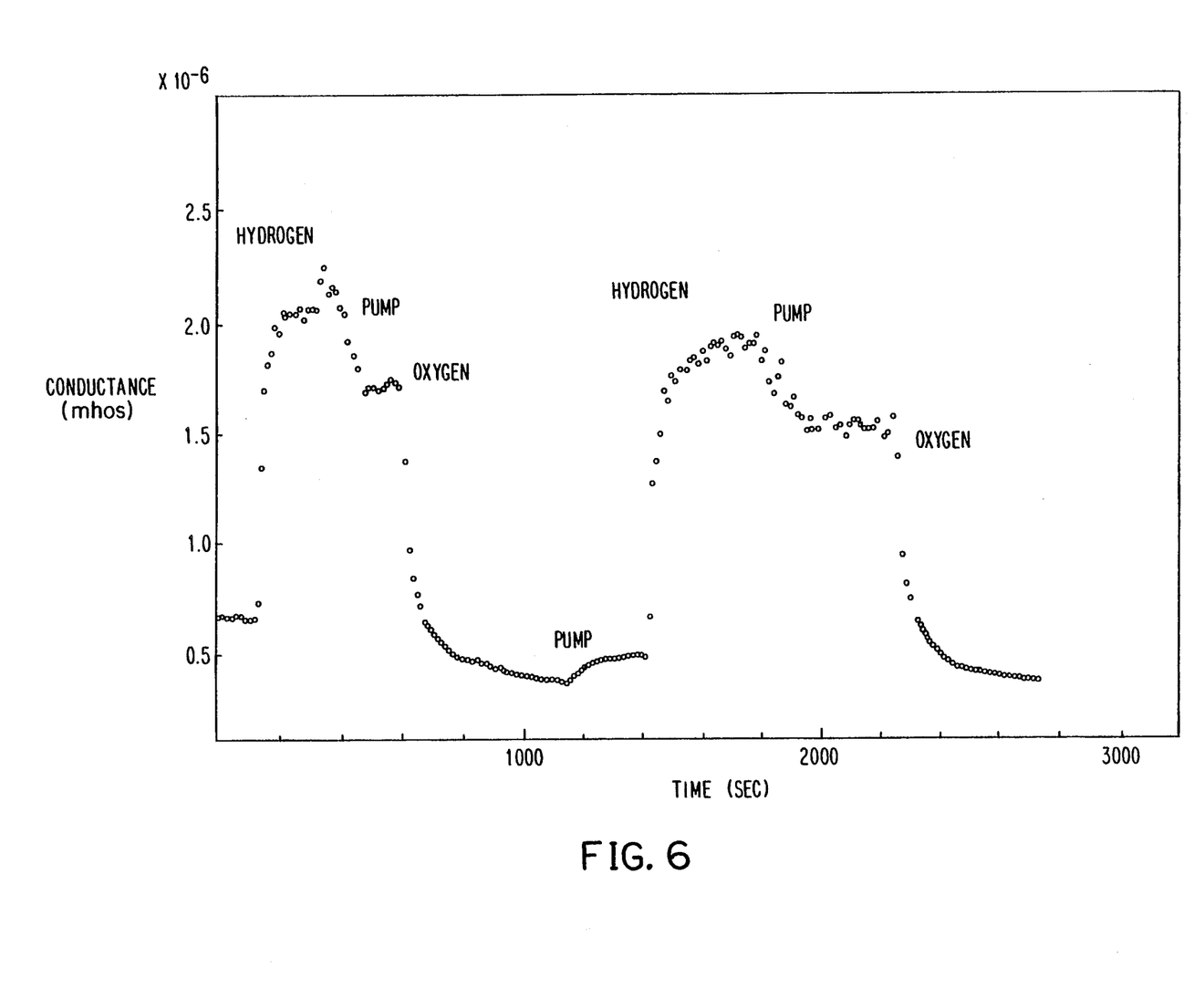
FIG. 6 is a plot of sensing results (conductance change) measured for injections of hydrogen and oxygen into a vacuum system with a $SnO_2$ sensor element held at 350° C.

The gas sensing response measured from an annealed $SnO_2$ film on a single pixel is illustrated in FIG. 6 These response tests were done with the array device shown in FIG. 6 mounted in the vacuum changer where the $SnO_2$ was deposited. The heating element of the pixel was heated using a current of approximately 12 mA which produced a temperature of 350° C. This temperature was sufficiently high to activate certain adsorptive reactions with gases and induce a sensing response as monitored by conductance changes in the $SnO_2$ film. Lower operating temperatures could be used for $SnO_2$ films which contain surface-dispersed metal additives, like Pd or Pt.

The conductance excursions in FIG. 6 from a vacuum base level illustrate the upward change produced when a reducing gas ($H_2$ at 1.3 Pa) and an oxidizing gas ($O_2$ at 1.3 Pa), respectively, are introduced into the vacuum. The plot is a unique signature of the annealed, 350° C. $SnO_2$ film.

An array for analyzing essentially any gas mixture can be obtained by providing a multiplicity of elements which are fabricated and/or post-processed and/or held at different temperatures. Each different element would then have a unique response when exposed to a gas or gas mixture. A signal matrix and pattern recognition or neuralnet procedures and signal deconvolution would be used to determine the composition and concentrations of the gases. While the application of a steady, controlled-matrix of operating temperatures could be applied to the multiple elements of an array sensor, certain benefits in operation could also be recognized by using temporally-defined temperature variations on some or all of the elements.

Single element temperature variations might be used to clean or regenerate a given element. They could also provide another response signature in the form of a signal vs temperature curve.

The size range for the pixels on which the individual sensing elements are constructed can be quite variable (perhaps from 1 cm to 50 microns or less on each side). At the smaller sizes, as many as 1000 devices could be fabricated on a chip. Heater currents, temperature measurement, and film measurement for the devices can be set and measured using on chip circuitry, because of the CMOS fabrication aspects of the array structure. On-chip multiplexers can be used to communicate signals off-chip. The analytical resolution for composition analysis of a mixture will depend on the number of different elements used in the sensing array as well as on the sophistication of the pattern recognition software used to analyze signals transmitted from the chip. The potential for large numbers of elements, easy control and measurement of the pixel temperature and properties and on-board circuitry means that self-calibration routines can be developed to produce advanced "smart" systems.

The extremely low mass possible (~0.2 $\mu g$) for the individual pixel sensors means that the temperature of each pixel can be controlled over a wide range (0° C. to 1200° C.) in an isolated way and changed very rapidly (~1 msec). While useful in constructing and processing the various integrated sensors (during film deposition and post-processing), these lightweight, fast-heating-/cooling features of the present invention make it extremely versatile in sensing operation. Each individually-addressed heater can be run to produce either a fixed matrix of temperatures in the array elements, or a dynamic matrix of temperature, where the temperature of each sensor element is varied according to its own particular schedule in time, which is selected and recorded. The low mass of the pixel-heater-sensing film components means that these schedules can include very fast temperature variations such as 1 msec temperature pulses at a high temperature, while monitoring film conductance response at a fixed lower temperature. In this way, kinetic response variations can be used in the chemical identification procedure. This fast temperature pulse concept can also be useful in studying the adsorption and sensing mechanisms from a scientific point of view. The fast temperature scheduling can also allow for fast "burnin" or cleaning periods during operation.

For use in certain harsh environments, sensing pixels could be coated with a protective layer which would protect the sensor underneath from adverse conditions. Heating a given sensor would cause its protective layer to volatilize or "burn off" thus exposing or "activating" the sensor element. When the performance of a given sensor or another "fresh" sensor are desired, the sensors could be activated as described. This embodiment, which could use for example a thin resinous protective layer could provide for hundreds of sensor elements to be installed in a hazardous environment and remotely activated sequentially over a long period of time.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

What is claimed is:

1. A temperature-controlled sensor element which comprises:
    a support substrate;
    a microbridge structure formed on said support substrate;
    a heating element formed on said microbridge structure so as to be thermally isolated from said support substrate;
    a conductive heat distribution plate formed above said heating element for evenly distributing heat from said heating element and;
    a layer of chemical active material formed above said conductive heat distribution plate.

2. A temperature-controlled sensor element according to claim 1, further including means to measure properties of said layer of chemical active material.

3. A temperature-controlled sensor element according to claim 2, wherein said means to measure properties of said layer of chemical active material comprises a plurality of contact pads beneath and in contact with said layer of chemical active material.

4. A temperature-controlled sensor element according to claim 1, wherein said conductive heat distribution plate includes four leads for sensing temperature.

5. A temperature-controlled sensor element according to claim 1, wherein a central portion of the microbridge structure is suspended over an etch pit which is formed in said substrate support.

6. A temperature-controlled sensor element according to claim 5, wherein said etch pit is formed with a closed bottom.

7. A temperature-controlled sensor element according to claim 1, wherein said chemical active material is adsorbent.

8. A temperature-controlled sensor element according to claim 1, wherein said chemical active material is catalytic.

9. A temperature-controlled sensor element according to claim 1, wherein said chemical active material is biologically active.

10. A temperature-controlled sensor element according to claim 1, wherein said conductive heat distribution plate is electrically conductive.

11. A temperature-controlled chemical sensor which comprises:
    an array of sensor elements positioned on a substrate support, wherein each of said sensor elements comprises:
    a microbridge structure formed on said support substrate;
    a heating element formed on said microbridge structure so as to be thermally isolated from said support substrate;
    a conductive heat distribution plate formed above said heating element for evenly distributing heat from said heating element and;
    a layer of chemical active material formed above said conductive heat distribution plate.

12. A temperature-controlled chemical sensor according to claim 10, wherein said chemical active material of each of said sensors is of the same material.

13. A temperature-controlled chemical sensor according to claim 11, wherein said chemical active material of each of said sensors is tuned to be responsive differently to a chemical species.

14. A temperature-controlled chemical sensor according to claim 10, wherein said chemical active material of each of said sensors is of a different chemical active material.

15. A temperature-controlled chemical sensor according to claim 10, wherein each of said heat distribution plates includes four leads for sensing temperature.

16. A temperature-controlled chemical sensor according to claim 10, wherein each of said sensor elements includes an etch pit beneath a central portion of its microbridge structure.

17. A temperature-controlled chemical sensor according to claim 15, wherein each of said etch pits includes a closed bottom.

18. A temperature-controlled chemical sensor according to claim 10, wherein said conductive heat distribution plate is electrically conductive.

19. A method of making a temperature-controlled sensor element which comprises:
    providing a support substrate having a first layer of an insulating material;
    forming a microbridge structure on said support structure;
    forming a heating element on said microbridge structure;
    forming a second layer of insulating material on said heating element;
    forming a conductive heat distribution plate on said second layer of insulating material;
    forming a third layer of insulating material on said conductive heat distribution plate; and forming a layer of a chemical active material on said third layer of insulating material.

20. A method of making a temperature-controlled sensor element according to claim 17, further comprising forming a plurality of contact pads beneath and in contact with said layer of chemical active material.

21. A method of making a temperature-controlled sensor element according to claim 17, which comprises forming a plurality of similar sensor elements on said substrate support.

22. A method of making a temperature-controlled sensor element according to claim 19, wherein each of said plurality of sensor elements is made to respond differently to a chemical species.

23. A method of making a temperature-controlled sensor element according to claim 17, further comprising forming said conductive heat distribution plate from an electrically conductive material.

24. A method of detecting components of a fluid mixture which comprises:
   providing a substrate having a plurality of micro-hotplates, wherein each of said plurality of micro-hotplates is provided with a conductive heat distribution plate and can be individually temperature controlled;
   providing a film of a chemical active material on each of said plurality of micro-hotplates;
   selectively heating said plurality of micro-hotplates while exposing said chemical active material to a fluid mixture; and
   measuring response of the chemical active material to said fluid mixture and determining therefrom the composition of said fluid mixture.

25. A method of detecting components of a fluid mixture according to claim 21, further comprising forming said conductive heat distribution plate from an electrically conductive material.

26. A method of detecting components of a fluid mixture according to claim 21, wherein said selectively heating comprises subjecting selective micro-hotplates to temperature variations.

27. A method of detecting components of a fluid mixture according to claim 21, further comprising regenerating the chemical active material after exposure by selectively heating said plurality of micro-hotplates above a regeneration temperature.

28. A method of detecting components of a fluid mixture according to claim 21, further comprising providing a protective layer over said chemical active material and selectively heating said plurality of micro-hotplates to burn off said protective layer and expose said chemical active material to said fluid mixture.

* * * * *